United States Patent [19]
Hossain et al.

[11] Patent Number: 4,828,912
[45] Date of Patent: May 9, 1989

[54] VIRUCIDAL PRODUCT HAVING VIRUCIDAL AND/OR GERMICIDAL PROPERTIES

[75] Inventors: Shafi U. Hossain; Kenneth R. Smith, both of Appleton, Wis.

[73] Assignee: Kimberly-Clark Corporation, Neenah, Wis.

[21] Appl. No.: 447,581

[22] Filed: Dec. 13, 1982

Related U.S. Application Data

[63] Continuation-in-part of Ser. No. 392,781, Jun. 30, 1982, abandoned, which is a continuation-in-part of Ser. No. 284,688, Jul. 20, 1981, abandoned.

[51] Int. Cl.⁴ .............................................. D04H 1/58
[52] U.S. Cl. .................................... 428/289; 428/284; 428/532; 428/537.1; 428/913
[58] Field of Search ................. 424/317, 28, 284, 289, 424/537, 913; 514/942

[56] References Cited

U.S. PATENT DOCUMENTS

| | | | |
|---|---|---|---|
| 967,688 | 8/1910 | Titterley | 424/28 |
| 2,688,586 | 3/1950 | Eberl et al. | 424/28 |
| 3,046,196 | 7/1962 | de Vaulchier | 424/28 |
| 3,141,821 | 7/1964 | Compeau | 167/58 |
| 3,317,376 | 5/1967 | Schattner | 424/28 |
| 3,650,964 | 3/1972 | Sedliar | 252/106 |
| 3,658,969 | 4/1972 | Vaille | 424/317 |
| 3,818,103 | 6/1974 | Von Esch | 424/317 |
| 4,045,364 | 8/1977 | Richter | 424/16 |

FOREIGN PATENT DOCUMENTS

| | | |
|---|---|---|
| 0008121 | 2/1980 | European Pat. Off. . |
| 1105549 | 4/1961 | Fed. Rep. of Germany . |
| 2312280 | 9/1974 | Fed. Rep. of Germany . |
| 1577926 | 10/1980 | United Kingdom .................. 424/28 |

OTHER PUBLICATIONS

Oxford et al., "Inactivation of Influenza and Other Viruses by a Mixture of Virucidal Compounds", Applied Microbiology, 21(10), 606–610, Apr., 1971.
Sagrosept Tucher Schulke and Mayr No. SH 144/12/82/10/1/2.
Sagrosept Tucher Schulke and Mayr No. SH 144/11/78/15/1/2.

*Primary Examiner*—James J. Bell
*Attorney, Agent, or Firm*—William D. Herrick

[57] ABSTRACT

Highly effective and useful method, composition and product for annihilating harmful respiratory viruses and inhibiting the spread of diseases, including the common cold. The product includes one or more carboxylic acids such as citric, malic, succinic, benzoic and the like in an effective amount and may also include a surfactant. Embodiments include impregnated or coated substrates such as facial tissue, nonwoven materials, and the like. In one application, treated tissue, when substituted for ordinary facial tissue and used in wiping the nasal area of a person suffering from a virus-borne infection is effective in annihilating the virus on contact with the treated tissue. This, in turn, prevents the spread of the virus-related illness.

27 Claims, No Drawings

VIRUCIDAL PRODUCT HAVING VIRUCIDAL AND/OR GERMICIDAL PROPERTIES

BACKGROUND OF THE INVENTION

1. Field of the Invention

This application is a continuation-in-part of our U.S. Pat. application Ser. No. 392,781 filed June 30, 1982 as a continuation-in-part of our U.S. patent application Ser. No. 284,688 filed July 20, 1981, both now abandoned.

This invention relates to a class of virucidal compositions highly efficacious against common respiratory viruses such as rhinoviruses, parainfluenza viruses, and adenoviruses and the methods and products utilizing such compositions. In particular, the invention relates to a novel type of virucidal composition which can be applied to a variety of substrates or carriers such as cellulosic webs, nonwoven structures, and textile-based materials. In addition, the class of virucidal compositions comprising this invention may also be incorporated into nasal sprays, facial creams, hand lotions, lipsticks, and similar cosmetic preparations. The compositions may also be used as ingredients in kitchen and bathroom cleansers, furniture and floor polishes, and similar household preparations.

Virologists knowledgeable in the field of respiratory viruses generally agree that rhinoviruses, influenza viruses, and adenoviruses are among the most important group of pathogenic agents which cause respiratory illnesses. Rhinoviruses, in particular, are thought to be the principle causative agent of what is generally known as "the common cold".

Rhinovirus, which causes cold symptoms, belongs to the picornavirus family. This family lacks an outer envelope, and, therefore, is characterized as "naked viruses". Although more than 100 different antigenic types of rhinoviruses are known, they share certain centrally important attributes. For instance, all are endowed with ether-resistant capsids, all are acid labile, and all contain single-stranded RNA (ca. $2.6 \times 10^6$ daltons). All are difficult to inactivate by common germicides such as quaternary ammonium compounds.

Adenoviruses include more than thirty antigenic types. When they invade the respiratory tract, they cause inflammation of the tissues leading to symptoms of pharyngitis, bronchitis, etc. While most adenovirus infections occur in childhood, infections of adults are far from uncommon. Like rhinoviruses, adenoviruses lack an envelope, (i.e. naked) but the adeno-nucleus, in contrast to the rhino-nucleus, contains a double-stranded DNA, and they are not characterized as acid labile. Adenoviruses are unusually resistant to inactivation.

Parainfluenza viruses, which belong to the paramyxovirus family, play an important role in the occurrence of lower respiratory diseases in children and upper respiratory diseases in adults. The parainfluenza viruses are RNA-containing viruses endowed with an ether-sensitive, lipoprotein envelope surrounding the nucleocapsid. These viruses are resistant to inactivation by carboxylic acids in low concentrations.

Recent work by Dick and others [Dick, E.C. and Chesney, P.J., "Textbook of Pediatric Diseases", Feigin, R.D. and Cherry, J.D. ed., Vol. II, pp. 1167–86(1981) W.B. Saunders Pub. Co., Phila., Pa.] has thrown considerable light on the mode of transmission of respiratory diseases caused by rhinoviruses. Although the exact mode of transmission of respiratory diseases is not fully understood, field studies by the above investigators have provided persuasive evidence that effective transmission of diseases such as common colds usually requires close association or contact—direct or indirect—between the infected subject and the potential victim. (Indirect contact may be looked upon as contact occurring via an intervening surface, e.g, table top, door knob, etc.) Thus, it may be possible to interrupt the chain of infection and reduce its potential to spread, if the viruses can be rendered ineffective as they emerge from an infected person's nose or mouth by immediate exposure to a virucidal agent. Moreover, after emergence, viruses which may ensconce themselves on the infected person's face or hands may also be "killed" if a suitable virucidal agent is quickly brought into contact with the appropriate anatomical surface, i.e., face, hands, etc. A facial tissue, containing a fast-acting, efficacious virucidal composition would offer a simple means of accomplishing the tasks mentioned above.

A long-felt need has existed for a safe and inexpensive virucidal agent effective against common respiratory viruses. Simple household germicides are not effective against rhino- and adenoviruses.

2. Description of the Prior Art

U.S. Pat. No. 4,045,364 to Richter discloses a disposable paper impregnated with an iodophor (i.e. iodine and a carrier) having germicidal properties and useful as a pre-wash in a surgical scrub routine. The patentee discloses that the stability of the iodophor is enhanced at a lower pH and that small quantities of weak organic acids such as citric acid or acetic acid can be added to achieve pH control. U.S. Pat. No. 3,881,210 to Drach et al describes a pre-moistened wiper for sanitary purposes which can include a bactericide. U.S. Pat. No. 3,654,165 to Bryant et al discloses a cleaner/sanitizer for wiping purposes including iodine providing bactericidal action. U.S. Pat. No. 3,567,118 to Shepherd et al discloses a fibrous material for cleaning purposes having a coating of a hydrophilic acrylate or methacrylate containing, inter alia, a bactericide.

While the prior art has disclosed that iodine compositions and products have a wide-spectrum virucidal effect, there has yet to be developed commercially an inexpensive product that successfully interrupts the spread of viruses such as rhinovirus or influenza virus. Problems with iodine result, for example, from its toxicity, and the fact that it is an irritant for animal tissue. The action of iodine is non-selective as between bacterial and mammalian protein, and its uncontrolled use upon the skin may cause severe irritation. Further, its activity may be diminished or neutralized by the action of biological fluids such as blood serum. Efforts to modify iodine to avoid these difficulties have not been completely successful.

References exist in the literature on the bactericidal action of acids such as citric, [e.g., Reid, James D., "The Disinfectant Action of Certain Organic Acids", *American Journal of Hygiene*, 16, 540–556 (1932)]. However, virucidal action is fundamentally different from bactericidal action in that viruses and bacteria represent different microorganisms with different characteristics. For instance, viruses do not replicate outside host cells whereas bacteria do. Quaternary ammonium compounds such as benzalkonium chloride are often effective against bacteria but not against viruses such as the various rhinoviruses.

Although it is known that rhinoviruses are labile to aqueous solutions of acids under low-pH conditions [e.g. Davis, B.D. et al; "Microbiology" pp. 1279–1306, at p. 1303. Harper E. Row (Publishers) New York, 1973 and Rueckert, R.R., "Picornaviral Architecture" Comparative Virology—Academic Press, New York (1971), pp. 194–306], known references do not mention the utilization of this concept in epidemiological contexts such as interruption of the chain of infection caused by rhinoviruses. To the best of our present knowledge the only systematic study of the virucidal action of organic acids (citric, malic, etc.) which exists in the generally available literature, was carried out by Poli, Biondi, Uberti, Ponti, Balsari, and Cantoni [Poli, G. et al: "Virucidal Activity of Organic Acids" *Food Chem.* (England) 4(4)251-8 (1979)]. These workers found that citric, malic, pyruvic and succinic acids, among others, were effective against herpesvirus, orthomyxovirus and rhabdovirus (Rabies virus). Their experiments were carried out at room temperature with aqueous solutions of pure acids. No substrate or carrier was used. The three viruses chosen for study by these workers were all "enveloped" viruses, resembling, in that regard, parainfluenza 3. Poli et al also observed that these acids were not effective against adenovirus which, it will be recalled, is a "naked" virus. Based on this, they concluded that these acids were effective against "enveloped" viruses but not against "naked" viruses.

It is known to those skilled in the art that adenoviruses are resistant to acids.

G. Poli et al., *Archiv fur Lebensmittelhygiene,* 29, 94–96 (1978) report a strain of adenoviruses to be susceptible to certain disinfectant surface active agents in aqueous solution. There is no suggestion, however, of combining such disinfectant surface active agents with an organic acid or with a substrate or carrier.

SUMMARY

The present invention provides a virucidal composition, the method of use and the product therefor which are highly effective over a broad spectrum of viruses and yet can be produced and used with safety. We have discovered that when at least one or more genus of a respiratory virus is contacted with an effective amount of a virucidal composition comprising a carboxylic acid having the formula R—COOH and explained hereinbelow in greater detail, the virus is substantially inactivated thereby interrupting and preventing the spread of the virus. These acids, which may be used in combination with a surfactant as discussed below, inactivate certain respiratory viruses, enveloped (e.g. parainfluenza) and naked (e.g. rhinovirus and adenovirus). A suitable carrier or substrate, such as facial tissue or a nonwoven web, incorporating such compositions is particularly useful in preventing the spread of virus. In general, these compositions and products can be handled without difficulty and are not believed to have any harmful effects when used in accordance with the invention. The compositions have little or no deleterious effects on color, odor, strength, or other important properties of the substrate or carrier. The products, for example, may be used as a dry wipe or maintained moist and used as a wet wipe.

DESCRIPTION OF THE PREFERRED EMBODIMENTS

While the invention will be described in connection with preferred embodiments, it will be understood that it is not intended to limit the invention to those embodiments. On the contrary, it is intended to cover all alternatives, modifications and equivalents as may be included within the spirit and scope of the invention as defined by the appended claims.

The present invention results from the unexpected discovery that certain acids such as citric, malic, succinic, and benzoic, used in suitable concentrations, as further described herein, are highly efficacious against rhinoviruses 16, 1A, and 86. When used in the presence of a surfactant such as sodium dodecyl sulfate (SDS), these acids were found to be effective also against parainfluenza 3 and adenovirus 5. In general, the water soluble carboxylic acids useful in accordance with the invention have the following structure:

R—COOH

Wherein R may be represented by: lower alkyl; substituted lower alkyl; hydroxy lower alkyl (e.g. HOCH$_2$—); carboxy lower alkyl (e.g. HOOC—CH$_2$—CH$_2$—); carboxy, hydroxy lower alkyl (e.g., HOOCCH$_2$CHOH—); carboxy, halo lower alkyl (e.g. HOOCCH$_2$CHBr—); carboxy, dihydroxy lower alkyl (e.g. HOOC—CHOH—CHOH—); dicarboxy, hydroxy lower alkyl

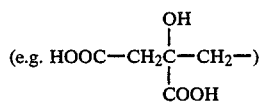

lower alkenyl, carboxy lower alkenyl (e.g. HOOCCH=CH—), dicarboxy lower alkenyl

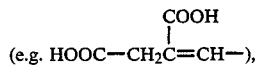

phenyl (C$_6$H$_5$—); substituted phenyl (e.g. hydroxy phenyl HO—C$_6$H$_4$—). Other acid examples include hydroxy lower alkyl e.g. lactic; carboxy, hydroxy lower alkyl, e.g. 2-methyl malic; carboxy, halo lower alkyl, e.g. 2-chloro-3-methyl succinic; carboxy, dihydroxy lower alkyl, e.g. 2-methyl tartaric; dicarboxy, hydroxy lower alkyl, e.g. 2-methyl citric acid; and carboxy lower alkenyl, e.g. fumaric. The above definitions are used in an illustrative but not a limiting sense. The term "lower" as used herein refers to an acid where "R" contains one to six carbon atoms. The term "substituted" indicates that one or more hydrogen atoms are substituted by halogen atoms (F, Cl, Br, I) hydroxyl groups, amino groups, thiol groups, nitro groups, cyano groups, etc.

The surfactant may be nonionic (e.g., the polyoxyethylenated alkylphenols such as TRITON X-100®, manufactured by Rohm and Haas; the polyoxyethylenated sorbitol esters such as TWEEN 40®, manufactured by ICI United States, Inc.), cationic (e.g. cetylpyridinium chloride (C$_5$H$_5$N$^+$(CH$_2$)$_{15}$CH$_3$ Cl$^-$), methylbenzethonium chloride (Me₃CCH₂C(Me)₂C₆H₃(Me)—OCH₂C-
H₂OCH₂CH₂⁺N(Me)₂CH₂C₆H₅ Cl⁻))

or anionic (e.g., sodium dodecyl sulfate, $(CH_3(CH_2)_{10}$—$CH_2OSO_3$—Na), the 1,4-bis (2-ethylhexyl) ester, sodium salt of sulfosuccinic acid, as manufactured by American Cyanamid Company under the tradename of AEROSOL OT). The preferred anionic surfactants may be represented by the structures:

1. $(ROSO_3)_x M^+$ or $(RSO_3)_x M^+$ wherein, $M^+$ is a mono, di or trivalent metal cation or an ammonium or substituted ammonium ion; x is an integer; and R is an alkyl group.

2. $M^+ \left( -O_3S - \underset{\underset{CH_2CO_2R_1}{|}}{CHCO_2R_2} \right)_x$ wherein, $M^+$ and x are defined as above and $R_1$ and $R_2$ may be the same or different and may be represented by straight or branched chain aliphatic groups. The above anionic surfactants are presented in an illustrative rather than a limiting sense. Surfactants, in general, are not virucidal with respect to naked viruses such as rhinovirus.

Although the invention is not limited to the use of a cellulosic web (such as facial tissue, bathroom tissue, hand towels for washroom and other uses and the like) as the substrate or carrier for the virucidal agents, a facial tissue impregnated with these novel virucidal agents sufficiently illustrates the underlying principle and represents a simple and useful embodiment of the invention. For this reason, the experiments described in the paragraphs which follow were carried out using facial tissues as the substrate. Examples of suitable nonwoven substrates are wet wipe materials such as wet-creped hand towels and spunbonded and meltblown polymeric webs commonly used in production of disposable hospital items such as surgical drapes, gowns, bedsheets, pillowcases, and the like. Other examples of nonwovens include composites of natural and/or synthetic fibers, formed by turbulent admixing, in nonwoven form. Textile materials of all types, including laminates of different materials, may be used as suitable substrates. For example, hygienic face masks used by persons suffering from respiratory illnesses provide an excellent means for utilizing the present invention. Other essentially inert carriers i.e., those which are essentially non-toxic and non-irritating to human or animal tissue under the conditions of normal use, will be apparent to those skilled in the art for applications such as lotions, sprays, creams, polishes and the like.

In general terms, the experimental procedure for preparing the samples in the examples below was simple and straightforward. Three-ply KLEENEX® facial tissues (11 inches×12 inches; basis weight: ca. 26 lb/2880 ft.² for all three plies combined) were impregnated with aqueous solutions of citric, malig., succinic, and benzoic acids by simple dipping. The acids were used either singly or as homogeneous mixtures. Usually the impregnating solution also contained a small percentage of a surfactant such as Aerosol-OT - [sodium salt of 1,4-bis(2- ethylhexyl) ester of sulfosuccinic acid, manufactured by American Cyanamid], or sodium dodecyl sulfate. In certain instances, a small amount of glycerol was also used to enhance tissue softness. The saturated tissues were pressed between rolls to squeeze out excess saturant and ensure uniformity of saturation. The tissues were weighed, dried, and the degree of saturation (i.e. percent saturant pick-up) was computed. The tissues were then ready for the testing of virucidal efficacy.

The procedure adopted for testing virucidal efficacy is in accord with standard virological assay techniques ($TCID_{50}$) with simple variations necessitated by the presence of the cellulosic substrate. A description of the procedure follows:

VIRUCIDAL ASSAY PROCEDURE

I. Materials

A. Solutions

| 1. Neutralizing Solution | 6.4 ml | 2 M Na₂HPO₄ |
|---|---|---|
| | 1.2 ml | 1.0 M Citric Acid |
| | 92.4 ml | 1× Medium 199 (nutrient medium for tissue culture) |
| 2. Hanks' - McIlvaine Salt Solution (HMSS): | | |
| | 2.0 ml 1.0 Citric Acid | Diluted to 2 liters with Hanks' Balanced Salt Solution. |
| | 18.0 ml 2.0 M Sterile Na₂HPO₄ | |
| | The pH of this solution is 7.0 | |
| 3. Hanks' Balanced Salt Solution: | | |
| | | g/liter in double-distilled water |
| NaCl | | 8.0 |
| KCl | | 0.4 |
| MgSO₄.7H₂O | | 0.2 |
| CaCl₂ (anhydrous) | | 0.14 |
| Na₂HPO₄.2H₂O | | 0.06 |
| KH₂PO₄ (anhydrous) | | 0.06 |
| Glucose | | 1.0 |
| Phenol red | | 0.005 |
| NaHCO₃ | | 0.35 |

Note:
The above solutions are not virucidal.

B Viruses and Tissue Culture Cell Lines

1. Rhinovirus type 16, type 1A and type 86: Rhinovirus types 16, 1A, and 86 (RV 16, 1A and 86 respectively) are grown in Ohio State HeLa (O-HeLa) tissue culture cells and stored at −60° F. until they are used. The virucidal testing involving the rhinoviruses is done using O-HeLa tissue culture test tubes incubated on a roller drum apparatus at 33° C.

2. Parainfluenza type 3: Parainfluenza type 3 (Para 3) grown in rhesus monkey kidney tissue culture cells and stored at −60° F. until it is used. The virucidal testing involving Para 3 virus is done using O-HeLa tissue culture test tubes incubated in a stationary position at 33° C.

3. Adenovirus type 5: Adenovirus type 5 (Adeno 5) is grown in HEp-2 tissue culture cells and stored at 60° F. until it is used. The virucidal testing involving adeno 5 virus is done using Human Epitheleal Carcinoma—2 (HEp-2) tissue culture test tubes incubated in a stationary position at 37° C.

II. Methods

A. Virucidal Testing

A 1:1 (volume:volume) mixture of virus and saliva is prepared. A one-square inch sample is cut out of treated Kimberly-Clark KLEENEX® tissue and placed in a plastic Petri dish. (A treated tissue is tissue impregnated with the virucidal agent under investigation.) The virus—saliva mixture (0.1 ml) is pipetted directly onto the sample and allowed to react for one minute. Note this is a two-fold virus dilution. After the reaction time of one minute, 5 ml of neutralizing solution is pipetted onto the sample in the Petri plate and agitated for 3 seconds. This is now a 100-fold virus dilution. The neutralizing solution—virus—saliva mixture is then pipetted out of the Petri plate and added to a tube containing 5 ml of Hanks' - McIlvaine Salt Solution. The sample is added to the same tube by tipping the plate and using the tip of a pipette to push it into the tube. The tube containing the 10 ml of solutions and the sample is vortexed for 30 seconds. This tube contains a $10^{-2.3}$ or 1:200 dilution of virus. Ten-fold serial dilutions (fresh pipette for each dilution) are made from the $10^{-2.3}$ dilution by taking 0.3 ml of the previous dilution and adding it to 2.7 ml of Hanks' - McIlvaine Salt Solution. 0.1 ml is inoculated into each tissue culture test tube. Generally two tubes are inoculated per dilution.

For each experiment two sets of controls are used. The first may be termed "the virus control" as it is designed to check the infectivity of the virus suspension itself without saliva or the tissue substrate. The virus suspension is diluted serially 10-fold in HMSS. 0.1 ml of specific dilutions are inoculated per tissue culture cell test tube. The information obtained from this control gives the number of infectious virus units that are contained in the virus solution that has been stored at -60° F. and insures that the aliquot of virus solution used in the experiment has not lost infectivity during the freezing, storage, or thawing processes.

The second control, "the tissue control", consists of performing the virucidal testing experiment using one square inch of an untreated KLEENEX® tissue. The information obtained from this control gives the number of infectious virus units that can be recovered from an untreated one inch square wipe following the virucidal testing procedure. The inoculated tissue culture tubes are examined for seven days for evidence of viral infection.

The endpoint of a virucidal test for a given wipe is that dilution of virus which infects actually or is calculated to infect only one of the two inoculated tubes. This number is defined as tissue culture infective dose, or $TCID_{50}$. The results of the virucidal activity of a given wipe are usually given as the "log difference" between the common log of the $TCID_{50}$ result of the treated sample subtracted from the common log of the $TCID_{50}$ of the untreated sample.

The virucidal efficacy of a sample may be derived from the "log difference" in the following manner:

$$\text{Virucidal Efficacy} = \left(\frac{X - Y}{X}\right) 100\%$$

Where:
X = the initial concentration of the virus (infectious units/0.1 ml) of untreated sample used as control.
Y = the final concentration of the virus (infectious units/0.1 ml) of the treated sample.

The following examples explain the computation procedure. (In the experiments, the final virus concentration was always less than or equal to $10^{2.3}$ infectious units/0.1 ml.) For the majority of the results, the final virus concentration was less than $10^{2.3}$. With an initial virus concentration of $10^{6.3}$, this would signify a log difference greater than 4 and a "kill" of greater than 99.99%).

1. Initial Concentration: $X = 10^{6.3}$
   Final Concentration: $Y = 10^{2.3}$
   Log Difference = (log $10^{6.3}$ − log $10^{2.3}$) = 4

$$\text{Virucidal Efficacy} = \left(\frac{10^{6.3} - 10^{2.3}}{10^{6.3}}\right) \times 100\%$$

$$= \left(\frac{10^{2.3}(10^4 - 1)}{10^{6.3}}\right) \times 100\%$$

$$= 99.99\%$$

2. Initial Concentration: $X = 10^{4.8}$
   Final Concentration: $Y = 10^{2.3}$
   Log Difference = 2.5

$$\text{Virucidal Efficacy} = \left(\frac{10^{4.8} - 10^{2.3}}{10^{4.8}}\right) \times 100\%$$

$$= 99.7\%$$

The proceduee outlined above is in conformity with standard microbiological assay techniques. It yields reliable and reproducible results within the limits of variability associated with biological experiments.

RESULTS

The results are shown in Tables I, II, and III. The data in Table I show that simple organic carboxylic acids such as citric, malic, tartaric, succinic and substituted derivatives thereof (e.g. 2-bromo-succinic), and benzoic acid and its substituted derivatives (salicylic acid), used in a facial tissue in suitable concentrations, are highly virucidal against rhinovirus 16 and parainfluenza 3.

Furthermore, the data in Table I show that, when used in conjunction with a surfactant such as Aerosol OT or sodium dodecyl sulfate, the concentrations of the acids in the facial tissue may be lowered without sacrificing virucidal efficacy.

Table II lists the results of experiments with acid mixtures chosen from the group citric, benzoic, succinic, and malic. The data show that the facial tissues treated with the acid mixtures are virucidal against rhinovirus 16 and parainfluenza 3. The data on Table II show that the facial tissue impregnated with a mixed acid system such as citric and malic and an appropriate surfactant such as SDS, is efficacious against rhinovirus 16, 1A and 86 and adenovirus 5. As these examples demonstrate, in accordance with the present invention, simple organic acids such as citric/malic/succinic, when used in conjunction with a suitable surface-active agent such as SDS, are highly virucidal against common respiratory viruses of which rhinovirus 16, 1A and 86, parainfluenza 3, and adenovirus 5 are typical examples. In addition, products using facial tissues as the means of deployment of the virucidal compositions mentioned are highly effective.

The significance of the invention resides in the fact that it provides the basis for interrupting the chain of infection caused by respiratory viruses. As viruses do not replicate outside the host cell, the degree of inactivation demonstrated in the experiments offers a simple and practical means of reducing the virus concentration in the vicinity of a person infected with a respiratory virus. This, in turn, significantly reduces the potential of the infection to spread.

summarized in Table IV. In general, the acid compositions within the scope of the invention are virucidally

TABLE I

VIRUCIDAL EFFICACY OF SINGLE ACIDS AGAINST RHINOVIRUS 16 AND PARAINFLUENZA 3 VIRUS (EXPOSURE TIME OF ONE MINUTE)

| Example No. | Virucidal Composition[a] | Surfactant[a] | Virucidal Efficacy Rhinovirus 16 | Parainfluenza 3 |
|---|---|---|---|---|
| 1 | Citric Acid (23.2%) | None | >99.99% | >99.7% |
| 2 | Citric Acid (18.7%) | None | >99.99% | |
| 3 | Citric Acid (9.7%) | AOT[b] (1%), SDS[c] (1%) | 99.99% | |
| 4 | Citric Acid (9.4%) | SDS (1%) | >99.99% | >99.99% |
| 5 | Succinic Acid (20%) | None | >99.99% | |
| 6 | Succinic Acid (9.1%) | SDS (2%) | >99.99% | >99.99% |
| 7 | 2-Bromosuccinic Acid (10.4%) | SDS (1%) | >99.99% | |
| 8 | Malic Acid (9.4%) | AOT (0.5%) | 99.99% | >99.99% |
| 9 | Tartaric Acid (15%) | None | >99.99% | |
| 10 | Benzoic Acid (30%) | None | >99.99% | |
| 11 | Salicyclic Acid (18%) | None | >99.99% | |
| 12 | Salicyclic Acid (9%) | None | >99.99% | |

[a]The figures in parentheses represent percent chemical used based on the weight of the facial tissue.
[b]AEROSOL OT ®, the sodium salt of the 1,4-bis (2-ethylhexyl) ester of sulfosuccinic acid.
[c]Sodium dodecyl sulfate.

TABLE II

VIRUCIDAL EFFICACY OF MIXED ACIDS AGAINST RHINOVIRUS 16 AND PARAINFLUENZA 3 VIRUS (EXPOSURE TIME OF ONE MINUTE):

| | Virucidal Composition* | | | | | Virucidal Efficacy | |
|---|---|---|---|---|---|---|---|
| Example No. | Citric Acid | Benzoic Acid | Malic Acid | Succinic Acid | Surfactant[a] | Rhinovirus 16 | Parainfluenza 3 |
| 13 | 10.7 | 0.2 | — | — | AOT[b] (1) | >99.99 | >99.97 |
| 14 | 10.3 | 0.2 | — | — | AOT (1) | >99.99 | >99.97 |
| 15 | 10.1 | 0.2 | — | — | AOT (1) | >99.99 | >99.97 |
| 16 | 7.1 | 0.2 | — | — | AOT (1) | >99.99 | >99.99 |
| 17 | 8.8 | 0.2 | — | — | AOT (1) | >99.99 | >99.99 |
| 18 | 10.3 | — | — | 5.2 | AOT (1) | >99.99 | >99.97 |
| 19 | 10.0 | — | — | 5.0 | AOT (1) | >99.99 | >99.97 |
| 20 | 10.0 | — | — | 5.0 | AOT (1) | >99.99 | >99.97 |
| 21 | 10.4 | — | 5.2 | — | AOT (1) | >99.99 | >99.99 |
| 22 | 10.5 | — | 5.3 | — | AOT (1) | >99.99 | >99.97 |
| 23 | 10.3 | — | 5.2 | — | AOT (1) | >99.99 | >99.97 |
| 24 | 10.2 | — | 5.1 | — | AOT (1) | >99.99 | >99.97 |
| 25 | 11.1 | — | 5.6 | — | AOT (0.5) | >99.99 | >99.7 |
| 26 | 10.6 | — | 5.3 | — | AOT (1) | >99.99 | >99.7 |
| 27 | 11.1 | — | 5.6 | — | AOT (0.5) | >99.99 | >99.7 |
| 28 | 10.6 | — | 5.3 | — | AOT (1) | >99.99 | >99.70 |
| 29 | 4.8 | — | 4.8 | — | AOT (1) | >99.99 | >99.99 |
| 30 | 13.8 | — | — | 5.0 | TX 100[c] (2) | >99.99 | >99.99 |
| 31 | 5.7 | — | 5.7 | — | SDS[d] (2) | >99.97 | >99.90 |
| 32 | — | 0.2 | 9.7 | — | SDS (2) | 99.97 | >99.90 |

[a]The figures in paraentheses represent percent chemical used based on weight of the facial tissue.
[b]AEROSOL OT ®
[c]TRITON X-100 ®
[d]Sodium dodecyl sulfate
*The figures represent percent chemical used based on the weight of the facial tissue.

TABLE III

VIRUCIDAL EFFICACY OF MIXED ACIDS AND SDS AGAINST RHINOVIRUS 16, RHINOVIRUS 1A, RHINOVIRUS 86 AND ADENOVIRUS 5 (EXPOSURE TIME OF ONE MINUTE)

| | Virucidal Composition[a] | | | Virucidal Efficacy | | | |
|---|---|---|---|---|---|---|---|
| Example No. | Citric Acid | Malic Acid | Surfactant SDS[b] | Rhinovirus 16 | Rhinovirus 1A | Rhinovirus 86 | Adenovirus 5 |
| 33 | 10.8 | 5.5 | 2.2 | >99.99 | — | — | 99.90 |
| 34 | 11.2 | 5.7 | 2.3 | >99.99 | — | — | 99.90 |
| 35 | 11.4 | 5.8 | 2.3 | >99.99 | — | — | 99.70 |
| 36 | 10.8 | 5.5 | 2.2 | >99.99 | — | — | 99.99 |
| 37 | 11.2 | 5.7 | 2.3 | >99.99 | — | — | 99.99 |
| 38 | 10.0 | 5.0 | 2.0 | >99.99 | >99.9 | >99.9 | 99.90 |

[a]The figures represent percent chemical used based on the weight of the facial tissue.
[b]Sodium dodecyl sulfate.

In order to more specifically illustrate the improved effects obtained in accordance with the invention, additional examples were carried out varying the concentration of selected acid compositions and measuring virucidal activity at one and five minutes. These results are effective to a high degree e.g., in the case of rhinoviruses or parainfluenza viruses, they produce a log drop of 2 or greater inactivation in one minute or less. For adenoviruses the time will be five minutes or less. In general, the degree of inactivation is greater after five minutes than after one minute as would be expected. Certain minor inconsistencies appear in the reported results due to the margin of error and the nature of the test procedure. It will be recognized by those skilled in this art that effectiveness is also influenced by the amount of the composition available for contact with the virus which, in turn, depends on the nature of the carrier. For example, as shown in Table IV, below, a relatively thick carrier with large voids such as wool may be ineffective unless treated with large amounts of the composition. On the other hand, a lightweight, relatively closed structure such as tissue or nonwoven material will require less of the composition. Based on the tests described, however, the effectiveness of a given combination of composition and carrier may be determined. For example, as shown in Table IV, citric acid is effective at concentrations tested from 5% to 10% add-on. The procedure used is described below.

For these examples $TCID_{50}$ results were obtained using WI-38 cells of low passage from Flow Laboratories, Inc. which were initially passed at least once to insure growth potential. The bottles were then split 1:2 and seeded in 96-well cluster tissue culture plates with a flat bottom growth area of 0.32 $cm^2$ obtained from M A Bioproducts. The cells were incubated at 37° C. in 5% $CO_2$ and, after 24 hours, were usually 80 to 90% sheeted and normal in appearance before use in the assay. The medium (2% MM) used for both dilutions and maintenance of the cells was MEM Eagles with Earles BSS (with glutamine, gentamicin sulfate and 2% fetal calf serum added). Rhinovirus 1A was obtained from the National Institute of Allergy and Infectious Diseases, Bethesda, Md. A vial was grown in WI-38 cells and harvested after showing 4+ cytopathogenic effect (CPE) at 2 days post inoculation. The virus was harvested, aliquoted, and frozen at −70° C. and later titered in WI-38 cells in 96-well cluster plates.

For the assay, the medium was removed from the plates by placing sterile gauze between the plate and the cover and turning the plate over. All six wells used received 0.1 ml of 2% MM. To the wells which were to be used as cell controls, another 0.1 ml of 2% MM was added. To the cells which were to receive the compounds, 0.1 ml of the appropriate dilution of material was added to each of six wells. The stock virus was mixed 1:1 with 2% MM for the initial dilution. One hundred microml. of this virus dilution were then added to a treated disc in a Petri dish. The virus was applied evenly over a tissue disc using a microliter syringe. The virus was allowed to remain on the disc for 1 minute or 5 minutes, then 5 ml of 2% MM was added to the disc in the Petri dish and the disc was slightly agitated. The disc and the solution were removed and placed in a sterile tube and agitated by vortexing for 30 seconds, representing the first dilution. Three ten-fold dilutions were made from the original tube and 0.1 ml of all four dilutions were added to the mono-layered WI-38 cells. Six wells were used for each dilution. Untreated controls were tested at 1 and 5 minutes, with and without virus and a virus titration was also run with each assay. The plates were reincubated at 37° C. in 5% $CO_2$ for the duration of the test.

Acids such as sulfamic and phosphoric were also found to be virucidal. However, these acids have been found to degrade carriers such as tissue.

TABLE IV

| Example | Acid | Concentration % Add-On | Surfactant SDS - % Add-On | One Minute $TCID_{50}$ ($Log_{10}$) Treated Tissue | One Minute ≈Log Drop vs. Control | Five Minutes $Log_{10}$ ($TCID_{50}$) Treated Tissue | Five Minutes ≈Log Drop vs. Control | Virucidal Efficacy One Min. | Virucidal Efficacy Five Min. |
|---|---|---|---|---|---|---|---|---|---|
| | | | | | | | | (% Kill) | |
| 39 | Glycolic | 12 | — | <2.0 | >3.25 | <2 | >2.75 | >99.94 | >99.82 |
| 40 | Glycolic | 9 | — | <2.0 | >3.25 | <2 | >2.75 | >99.94 | >99.82 |
| 41 | Glycolic | 2.4 | — | <2.0 | >3.25 | <2 | >2.75 | >99.94 | >99.82 |
| 42 | Salicylic | 7.2 | — | <2.0 | >2.33 | <2 | >2.75 | >99.5 | >99.8 |
| 43 | Salicylic | 5.4 | — | <2.0 | >2.33 | <2 | >2.75 | >99.5 | >99.8 |
| 44 | Salicylic | 3.6 | — | ≧5.17 | 0 | 4.67 | 0.5 | 0 | 68 |
| 45 | Salicylic | 1.4 | — | ≧5.25 | 0 | ≧5.4 | 0 | 0 | 0 |
| 46 | Succinic | 9.2 | — | <2.0 | >3.25 | <2 | >2.75 | >99.94 | >99.82 |
| 47 | Succinic | 6.9 | — | <2.0 | >3.25 | <2 | >2.75 | >99.94 | >99.82 |
| 48 | Succinic | 4.6 | — | <2.0 | >3.0 | <2 | >3.17 | >99.9 | >99.93 |
| 49 | Succinic | 1.8 | — | 3.9 | 0.8 | 3.9 | 0.4 | 84 | 60 |
| 50 | Malic | 10.5 | — | <2.0 | >3.25 | <2.0 | >2.75 | >99.94 | >99.82 |
| 51 | Malic | 7.9 | — | NA | NA | <2.0 | >2.75 | NA | >99.82 |
| 52 | Malic | 5.2 | — | <2.0 | >3.25 | <2.0 | >2.75 | >99.94 | >99.82 |
| 53 | Malic | 2.1 | — | 2.38 | 2.87 | <2.0 | >2.75 | 99.9 | >99.82 |
| 54 | 2-Bromo-Succinic | 2.0 | — | 3.33 | 1.92 | <2.0 | >2.75 | 98.8 | >99.8 |
| 55 | 2-Bromo-Succinic | 10.2 | 2.0 | 2.5 | 2.5 | 2.5 | 2.67 | 99.7 | 99.8 |
| 56 | Tartaric | 11.7 | — | <2.0 | >3.25 | <2.0 | >2.75 | >99.94 | >99.82 |
| 57 | Tartaric | 8.8 | — | <2.0 | >3.25 | <2.0 | >2.75 | >99.94 | >99.82 |
| 58 | Tartaric | 5.9 | — | <2.0 | >3.25 | <2.0 | >2.75 | >99.94 | >99.82 |
| 59 | Tartaric | 2.3 | — | <2.0 | >3.25 | <2.0 | >2.75 | >99.94 | >99.82 |
| | | | | | | | | (% Inactivation of Rhinovovirus 1A) | |
| 60 | Maleic | 6.8 | — | <2.0 | >3.25 | a | a | >99.94 | a |
| 61 | Maleic | 4.5 | — | <2.0 | >3.25 | ≦2.0 | ≧2.75 | >99.94 | ≧99.8 |
| 62 | Maleic | 1.8 | — | 2.25 | ≧3.00 | <2.0 | >2.75 | 99.9 | >99.8 |
| 63 | Aconitic | 9.0 | — | <2.0 | >3.25 | <2.0 | >2.40 | >99.94 | >99.6 |
| 64 | Aconitic | 6.8 | — | ≦2.0 | ≧3.25 | <2.0 | >2.75 | ≧99.94 | >99.8 |
| 65 | Aconitic | 1.8 | — | 3.40 | 1.85 | 3.50 | 1.25 | 98.6 | 94 |
| 66 | Citric | 10.0 | — | <2.0 | >3.25 | <2.0 | >2.75 | >99.94 | >99.8 (2) |
| 67 | Citric | 7.5 | — | ≦2.0 | >3.25 | <2.0 | >2.40 | ≧99.94 | >99.6 |
| 68 | Citric | 5.0 | — | ≦2.0 | ≧3.25 | ≦2.0 | >2.75 | ≧99.94 | >99.8 (2) |
| 69 | Citric | 2.0 | — | 3.75 | 1.0 | <2.0 | >2.4 | 90 | >99.6 |

TABLE IV-continued

| Example | Acid | Concentration % Add-On | Surfactant SDS - % Add-On | One Minute | | Five Minutes | | Virucidal Efficacy | |
|---|---|---|---|---|---|---|---|---|---|
| | | | | $TCID_{50}$ $(Log_{10})$ Treated Tissue | ≈Log Drop vs. Control | $Log_{10}$ $(TCID_{50})$ Treated Tissue | ≈Log Drop vs. Control | One Min. | Five Min. |
| 70 | Phosphoric | 5.0 | — | <2.0 | >3.0 | <2.0 | >3.17 | >99.9 | >99.93 |
| 71 | Phosphoric | 3.8 | — | ≦2.0 | ≧3.0 | <2.0 | >3.17 | ≧99.9 | >99.93 |
| 72 | Phosphoric | 2.5 | — | ≦20 | ≧3.0 | <2.0 | >3.17 | ≧99.9 | >99.93 |
| 73 | Phosphoric | 1.0 | — | 4.25 | 0.75 | 4.40 | 0.77 | 82 | >83 |
| 74 | Citric/Malic | 10.0/5.0 | — | <2.0 | >1.75 | <3.0 | >1.40 | >98.2 | >96 |
| 75 | Citric/Malic | 10.0/5.0 | — | <2.0 | >3.0 | <2.0 | >3.17 | >99.9 | >99.93 |
| 76 | Wool substrate BW = 174.4 mg/sq. in) | | 0.6 mg/in² | 4.6 | 0.4 | NA | NA | 60.0 | NA |
| 77 | Meltblown Polypropylene facemask BW = 52.5 mg/in² | | 0.6 mg/in² | a | a | <3.0 | 1.6 | NA | >97.5 |

NOTE:
[a] in some cases particularly with addition of surfactant, cytopathic effects prevented useful data from being obtained. Such effects are described in Lennette, et al, Diagonistic Procedures for Viral, Rickettsial, and Chlamydial Infections, 1979, 5th Ed., p. 67.

TABLE V

| Example | Acid | μMole/in² | Acid Add-on % | Surfactant Add-on % | Virucidal Activity (% Inactivation of Rhinovirus 16) | |
|---|---|---|---|---|---|---|
| | | | | | 1 Min. | 5 Min. |
| 78 | Sulfamic | 15.6 | 5 | — | 99 | >99.997 |
| 79 | " | 46.8 | 15 | — | 99.997 | >99.997 |
| 80 | " | 15.6 | 5 | — | 99 | 99 |
| 81 | " | 15.6 | 5 | SDS 2% | 99 | >99.99 |

Because some of the acids are soluble in water, they can be applied to many substrates from an aqueous solution with great ease either by dipping, coating, or other conventional means such as spraying or gravure printing. The composition is applied to the substrate in an amount sufficient to provide virucidal activity as defined herein. It is understood that reference to a soluble acid means that the acid is sufficiently soluble so that it will produce a virucidal effect. As will be seen from the examples above, solubilities may range from high solubility (e.g. glycolic acid used in Examples 39-41) to low solubility (e.g. salicylic acid used in Examples 11, 12, and 42-45). While the lower effective limit for the acids has not been precisely determined, in general, for a substance such as facial tissue having a basis weight in the range of 23 to 31 lbs./2880 ft.² (3 ply), there should be a pick-up of at least about 2 percent and preferably about 5 percent of acids such as citric on a dry basis. Other substrates such as nonwovens may be utilized as well.

When mixtures of acids are employed, they may be in any proportion, but preferably the mixtures contain at least about 0.2 to 10% of each acid based on the weight of the substrate after drying.

When surfactants are included, they are preferably selected from the group of anionic surfactants and included in the amount of about 0.05 to 5% based on the weight of the substrate after drying.

In the application of the virucidally active organic acids defined herein in other substrates or carriers such as lotions, mouthwash, creams, sprays, polishes and the like, the preferred members being substantially non-toxic or non-irritatig upon contact with human or animal tissue, the virucidally effective amount may be determined readily upon application of the procedures set for herein. For example, a log drop of 2 or more would mean that 99 percent or more of the host viruses are inactivated upon contact with the acid compositions described and claimed herein.

Thus, it is apparent that there has been provided, in accordance with the invention, a virucidal product which, under conditions of normal use fully satisfies the objectives and advantages as set forth in the previous paragraphs.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations which fall within the spirit and broad scope of the appended claims.

We claim:

1. A virucidal product comprising,
   (a) a substrate selected from the group consisting of cellulosic webs and nonwoven webs,
   (b) said substrate containing a virucidally effective amount of a composition comprising,
      (i) from about 0.05 to about 5 weight percent, based on the dry weight of the substrate, of an anionic surfactant, and
      (ii) at least about 2 percent, based on the dry weight of the substrate, of at least one acid having the structure:

R—COOH wherein R is radical selected from lower alkyl radicals, or substituted derivatives of such acids selected from the group consisting of citric, malic, succinic, benzoic, and substituted derivatives thereof, and mixtures of two or more of said acids.

2. The product of claim 1 wherein said surfactant is selected from the group consisting of alkyl sulfonate salts, sulfuric acid eater salts and sulfosuccinic ester salts having a structure:

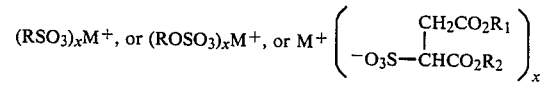

wherein $M^+$ is a mono, di or trivalent metal cation or an ammonium or substituted ammonium ion, x is an integer; and R is an alkyl group, $R_1$ and $R_2$ are the same or different straight or branched chain aliphatic groups.

3. The product of claim 1 wherein said surfactant is selected from the group consisting of alkyl sulfonate salts and alkyl sulfate salts.

4. The product of claim 1 wherein said surfactant is sodium dodecyl sulfate.

5. The product of claim 1 wherein R is selected from the group consisting of carboxy hydroxy lower alkyl; carboxy dihydroxy lower alkyl; and dicarboxy hydroxy lower alkyl groups.

6. The product of claim 1 wherein said acid is selected from the group consisting of citric acid, malic acid, succinic acid, benzoic acid, and mixtures of two or more of said acids.

7. The product of claim 1 wherein said acid is selected from the group consisting of citric acid, malic acid, and mixtures of citric acid and malic acid.

8. A product comprising,
   (a) a wholly or partially cellulosic facial tissue, and
   (b) said facial tissue containing a composition comprising,
      (i) from about 0.2 percent to about 10 percent, based on the dry weight of the tissue, of citric acid,
      (ii) from about 0.2 percent to about 10 percent, based on the dry weight of the tissue, of malic acid, and
      (iii) from about 0.05 to about 5 weight percent, based on the dry weight of the tissue, of an anionic surfactant present in an amount which is virucidally effective against rhinovirus, adenovirus, parainfluenza virus, and influenza virus and which is compatible with the physical properties of said tissue.

9. A product comprising,
   (a) a cellulosic substrate, and
   (b) said substrate containing a composition comprising
      (i) at least about 2 percent, based on the dry weight of the substrate, of citric acid and/or malic acid, and
      (ii) from about 0.05 to about 5 weight percent, based on the dry weight of the substrate, of an anionic surfactant present in an amount which is germicidal or virucidally effective against rhinovirus, adenovirus, parainfluenza virus, influenza virus, and which is compatible with the physical properties of said substrate.

10. A product comprising a cellulosic substrate, said substrate containing from about 0.05 to about 5 weight percent of an anionic surfactant, and at least 2 weight percent of acid selected from the group consisting of citric acid, malic acid, and a mixture of citric acid and malic acid.

11. The product of claim 10 wherein the acid is a mixture of citric acid and malic acid.

12. The product of claim 10 having at least about 2 dry weight percent citric acid and at least abouat 2 dry weight percent malic acid.

13. The product of claim 12 wherein the anionic surfactant is sodium dodecyl sulfate.

14. The product of claim 13 wherein said substrate is a facial tissue having about 10 dry weight percent citric acid, about 5 dry weight percent malic acid, and about 2 dry weight percent sodium dodecyl sulfate.

15. The product of claim 10 wherein the acid is citric acid.

16. The product of claim 15 wherein the anionic surfactant is sodium dodecyl sulfate.

17. The product of claim 16 wherein said substrate, is a facial tissue.

18. The product of claim 10 wherein the acid is malic acid.

19. The product of claim 18 wherein the anionic surfactant is sodium dodecyl sulfate.

20. The product of claim 19 wherein said substrate is a facial tissue.

21. A product comprising
   (a) a cellulosic substrate, and
   (b) said substrate containing a composition comprising at least about 2 percent, based on the dry weight of the substrate, of at least one acid having the structure:

   R—COOH alkyl wherein R is a radical selected from the group consisting of lower alkyl; substituted lower alkyl; carboxy lower alkyl; carboxy hydroxy lower alkyl; carboxy halo lower alkyl; carboxy dihydroxy lower alkyl; dicarboxy hydroxy lower alkyl; lower alkenyl; carboxy lower alkenyl; dicarboxy lower alkenyl; phenyl; and substituted phenyl radicals, present in an amount which is germicidal or virucidally effective against rhinovirus, parainfluenze virus, and influenza virus and which is compatible with the physical properties of said substrate.

22. The product of claim 21 wherein R contains from 1 to 6 carbon atoms.

23. The product of claim 21 wherein the acid is selected from the group consisting of citric, malic, succinic, benzoic, and mixtures of two or more of said acids.

24. The product of one of claims 1, 2, 3, 4, 5, 6, 7, or 21 wherein the substrate is a cellulosic facial tissue.

25. The product of claim 21 wherein the acid is citric acid.

26. The product of claim 21 wherein the acid is malic acid.

27. The product of claim 21 wherein the acid is a mixture of citric acid and malic acid.

* * * * *